United States Patent [19]

Ricci

[11] E Re. 31,372

[45] Reissued Sep. 6, 1983

[54] METHOD FOR MEASURING ANTISTREPTOLYSIN CONCENTRATION IN BLOOD

[75] Inventor: Antonio Ricci, Siena, Italy

[73] Assignee: Istituto Sieroterapico e Vaccinogeno Toscano "Sclavo" S.p.A., Siena, Italy

[21] Appl. No.: 252,219

[22] Filed: Apr. 8, 1981

Related U.S. Patent Documents

Reissue of:

[64] Patent No.: 4,148,609
Issued: Apr. 10, 1979
Appl. No.: 747,048
Filed: Dec. 2, 1976

[30] Foreign Application Priority Data

Dec. 22, 1975 [IT] Italy ..... 9660 A/75

[51] Int. Cl.[3] ..... G01N 33/54

[52] U.S. Cl. ..... 436/522; 23/915; 435/7; 436/520; 436/547

[58] Field of Search ..... 23/230 B; 424/12; 435/7

[56] References Cited

U.S. PATENT DOCUMENTS 3,789,116 1/1974 Kay ..... 424/8
3,925,161 12/1975 Galvani .
4,038,147 7/1977 Reno .

OTHER PUBLICATIONS

"Man. Clin. Immunol.," N. R. Rose et al., eds., Chapter 33 (264–273), G. C. Klein, Am. Soc. Microbiol., Washington, D.C., 1976.

Chemical Abstracts, 80:131627j (1974).

*Primary Examiner*—Sidney Marantz
*Attorney, Agent, or Firm*—Morgan, Finnegan, Pine, Foley & Lee

[57] ABSTRACT

A method for measuring the antistreptolysin concentration in a human blood sample by adding a solution of oxidized O-streptolysin to the blood sample (diluted), incubating, reacting with a reducing solution, incubating and relating the resulting hemolysis to the antistreptolysin concentration.

5 Claims, 5 Drawing Figures

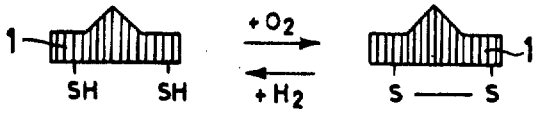
Fig.1
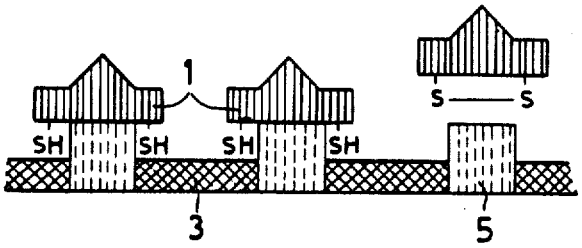
Fig.2
Fig.3
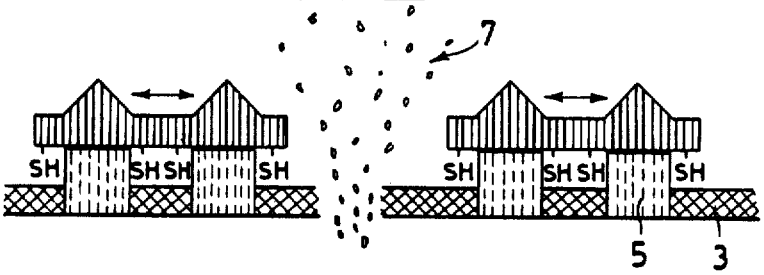
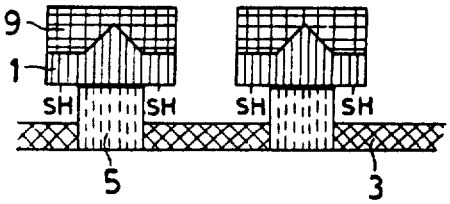
Fig.4
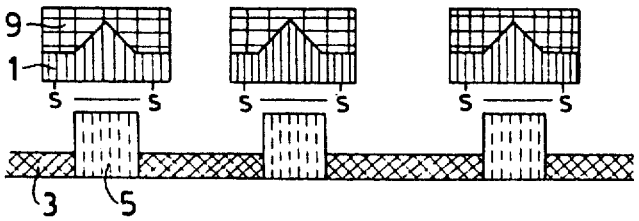
Fig.5

METHOD FOR MEASURING ANTISTREPTOLYSIN CONCENTRATION IN BLOOD

Matter enclosed in heavy brackets [ ] appears in the original patent but forms no part of this reissue specification; matter printed in italics indicates the additions made by reissue.

O-streptolysin (O-S) is a toxin of a proteinic nature, which is secreted by certain Streptococci of the A Group. This toxin is deadly for the test animals, destroys the cellular cultures, and lyses the red blood cells and the white cells of many animal species.

BRIEF DESCRIPTION OF THE DRAWINGS

FIG. 1 is a diagrammatic representation of O-streptolysin; and

FIGS. 2-5 are, respectively, diagrammatic illustrations of different stages in the action of O-streptolysin on red cells.

A few oxidants succeed in inhibiting the lytic power of this toxin. The alterations undergone by the molecules involve the sulfhydryl groups —SH which are converted into disulfide groups —S—S—. As a matter of fact, by adding a reducing substance, such as mercaptoethanol, the —SH groups are restored. The two reactions are shown in FIG. 1, wherein O-streptolysin (O-S) is indicated by a geometric FIG. 1 having vertical shading.

Hemolysis of the red cells, as incubated with the toxin at 37° C., takes place only if the O-S is in its reduced form, that is with the —SH groups, inasmuch as the oxidized toxin cannot act by the groups —S—S— with the cytoplasmic membrane of the red cells. The membrane receptor has been identified as cholesterol. FIGS. 2 and 3 diagrammatically show the phenomenon, the numeral 3 indicating the cytoplasmic membrane in cross-hatching, whereas the numeral 5 indicates, in common hatching, the membrane-receptor cholesterol. Only those molecules of O-S which are bound to the membrane receptors (see FIG. 2) interact with one another as indicated in FIG. 3, and arrange themselves in the form of circular channels or holes; hemoglobin 7, indicated with dots in FIG. 3, emerges through said holes or through other areas wherein the lipids have undergone a deorganization due to the cholesterol loss.

If O-S is allowed to be incubated with the red cells at +4° C., at this temperature the attack is experienced of O-S against the cholesterol of the red cells, but no lysis occurs, since the interaction between the toxin molecules is a function of temperature. Hemolysis occurs when the system is brought to 37° C. If anti-O-S (antistreptolysin) antibodies are added to the system at +4° C. and then the temperature is raised to 37° C., no hemolysis is experienced. The explanation is as follows:

The functional groups of the O-S which were intended to interact with one another have been blocked by the antibodies. The phenomenon is illustrated diagrammatically in FIG. 4, wherein the anti-O-S antibodies have been shown by domains 9.

If the oxidized O-S is allowed to be incubated with red cells at 37° C., no hemolysis occurs. As a matter of fact, the oxidized O-S cannot stick to the membrane receptors 5 (see FIG. 2). If anti-O-S antibodies 9 are added, these latter are bound to the oxidized O-S and the conditions of FIG. 5 are obtained.

By now adding a reducing substance to the system, the sulfhydryl groups —SH are restored but no hemolysis takes place, since the functional groups of O-S, intended mutually to interact, have been blocked by the antibodies 9 (see FIG. 4).

The following scientific articles are cited as regards the foregoing. In summary:

(1) Howard, J. F., Wallace, M. R.: Brit. J. Exp. Path. 34, 181 (1953);

(2) Rants, L. A., Randall, R.: Proc. Sec. Exp. Biol. Med. (N.Y.) 59, 22, (1945);

(3) Alan, J. E., Raymond, M.: Ann. Inst. Pasteur, 114, (1968).

A diagnostic method was suggested long ago for evaluating the magnitude of the presence of O-antistreptolysin antibodies.

There exists, in particular, in the trade, a diagnostic means which makes it possible to assay the antistreptolysin antibodies in the blood serum of patients, said means comprising the following materials for the reactions:

The serum to be tested, clear and inactivated at 56° C. for 30 minutes.

The physiological solution, buffered at a pH of 6.5.

The 5% suspension of rabbit red blood cells.

The reduced O-S which has perfectly been titrated at the lyophilic state.

Progressively increased dilutions of the serum to be tested are incubated at 37° C. during 15 minutes, with a constant amount of O-S. If antibodies are present, the attack of the antibodies against O-S takes place at this stage, the hemolytic activity of the O-S being thus neutralized. On completion of this procedure, 5% red blood cells are added in buffered solution, stirred and allowed to incubate at 37° C. during 45 minutes, then centrifuged at 2,000 rpm and the supernatants are read out. The antibody contents of the serum is given by the reciprocal of the higher serum dilution which inhibits the hemolytic activity of the O-S.

This method, which essentially consists in determining the hemolysis of the red cells added to the system by a possible excess of O-streptolysin, which has previously been reacted with a sample of blood serum deprived of complementary elements and taken from a patient, has, inter alia, the following drawbacks:

(1) Fresh serum, deprived of complementary elements is required, at 56° C. for 30 mins. (these requirements imply the initial drawl of the patient's blood, the holding of same at room temperature for two hours, the separation of the coagulum from the serum and its centrifugation, the inactivation of the serum complement at 56° C. during 30 mins.);

(2) It is necessary to have human red cells available (O Rh+group) or rabbit cells, washed and diluted at 5% (with a consequent cumbersomeness of the washing operations);

(3) The technique is cumbersome (especially the dilution of the serum, the addition of O-streptolysin and red cells to the diluted serum);

(4) A certain number of thoroughly washed pipettes and test tubes is required for the titration.

The novel method according to the invention exploits the following two known principles:

that the oxidized O-S is incapable of binding itself to the red cells (FIG. 2) but interacts with the specific antibodies (FIG. 5) and that the oxidized O-S after reduction reacquires its hemolytic power (FIG. 3).

According to the invention, and characteristically, the reaction is carried out by using the unstripped blood of the patient and by using the red cells as present therein as the detectors. The O-S that is supplied is oxidized and thus incapable of being bound to the red cells. As the oxidized O-S is put into contact with the patient's blood, if anti-O-S antibodies are present, the neutralization reaction of O-S takes place without attack upon the membrane. Subsequently, a reducing substance is introduced, which is capable of reducing just the oxidized sulfhydryls (—S—S—) of the toxin and restoring the —SH sulfhydryls so as to render the latter capable of being fixed to the red cells. At this stage, two distinct situations may occur:

(A) The O-S is not bound to antibodies due to the absence of the latter: if so, the O-streptolysin, once it has been reduced, is capable of being fixed to the red cells and deorganizing the membrane of the red cells and forming intermolecular chains, which gives rise to hemolysis, a fact which is easily detectable.

(B) The O-S is bound to the antibodies as contained in the blood (or serum) being tested. In this case the subsequent reduction could possibly enable the O-S to be attached to the free sulfhydryl positions of the cellular membrane of the red cells, but will be unable to form intermolecular chains which do not deorganize the red cell membrane and thus no hemolysis can be caused to occur.

On the basis of the foregoing, and more exactly, a first object of the present invention is to provide a device for determining the antistreptolysin rating of blood, which comprises: a basic product formed by oxidized O-streptolysin, in preselected concentrations, a reducing substance to restore the hemolytic capability of O-streptolysin with the sulfhydryl groups —SH, and a diluent for the patient's blood.

More particularly, the device comprises: a plurality of containers of oxidized O-streptolysin, with a solvent and/or uniform blood samples, with gradually decreasing dilutions, for samples of diluted blood of a constant volume.

A second object of the present invention is to provide a method for the determination of the antistreptolysin concentration, which substantially comprises the steps of contacting oxidized and reducible O-streptolysin with blood samples and the subsequent treating with a reducing substance to restore the hemolytic ability of the O-streptolysin.

More particularly, in the method according to the present invention, provisions are taken so that in containers which hold oxidized O-streptolysin in amounts and thus in dilutions which are graduated, there are introduced even dosage units of the blood to be tested, which have properly been so diluted that, to each container, a reducing substance is added so as to reinstate the hemolytic ability of O-streptolysin and to obtain the hemolysis, and the phenomenon is evaluated in the different containers upon incubation.

Broadly stated, the present invention provides a method for measuring the antistreptolysin concentration in a sample of human blood, characterized by the steps of:

(a) preparing a plurality of solutions of different concentrations of oxidized O-streptolysin;

(b) preparing a solution of a reducing substance selected from the group consisting of thiols, sodium metabisulphite and sodium sulphite, (c) diluting a blood sample with an appropriate nonhemolytic solution;

(d) introducing an equal volume of diluted blood in each of the solutions defined at (a) hereinabove, (e) incubating the solution resulting from (d) at a temperature between room temperature (18° C.–21° C.) and 50° C. for a time of the order of 15 minutes;

(f) adding to the incubated solution (e) a measured volume of solution (b);

(g) incubating the solution (f) at a temperature between room temperature and 50° C. for such a time as is necessary for the sedimentation of the red blood cells to occur, and (h) noting the sample containers in which no hemolysis has taken place.

The advantages of the method suggested herein as compared with the classical method as used nowadays are apparent and the principal ones are:

(1) Simplification of the technique, inasmuch as it is no longer necessary to separate the serum from blood or to proceed to strip the blood serum from its complements, a substantial reduction of the manipulations and the time taken for analysis being thus achieved.

(2) Dispensing with the red cells, the preparation of which is a considerable limitation upon the procedure, due to the difficulty of procuring the material and storing it and to the difficulty of its preparation.

(3) Reduction of both time and cost of the test, as a result of the smaller number of operations and the possibility of employing untrained personnel, on account of the extreme simplicity of the method.

(4) Possibility of using for the test very small blood samples, a fact which facilitates sampling in those occasions wherein this is made difficult by the special conditions of the patient.

The starting materials for the determination of the antistreptolysin rating are as follows:

blood, as such, of the patient, diluting solution for the blood, oxidized O-streptolysin, distributed into containers (test tubes) at different known concentrations, solution of reducing substance, such as: among the organic reducing substances: the thiols, such as mercaptoethanol, dithiotreitol, cystein, N-acetyl-cystein.

Among the inorganic reducing substances, for example: sodium metabisulfite, sodium sulfite.

Once the patient's blood has been sampled (on account of the small amount required, blood can be drawn also from the fingers of the upper limbs or the ear lobes), an appropriate dilution is carried out with a suitable dilution solution, by placing small quantities (such as 0.2 mls) in each container of a set of containers in which lyophilic oxidized O-streptolysin is already present in a determined quantity.

After a short period of incubation, for example 15 minutes at a temperature between room temperature and 50° C., a determined volume of the reducing substance is added and incubation is allowed to proceed at room temperature and up to 50° C., for the time which is necessary for the sedimentation of red cells to occur (for example 1–2 hours).

On completion, the hemolyzed and nonhemolyzed supernatants are read out by transparency: in substance, the containers in which no hemolysis occurred are noted. The antibody concentration in the tested samples, as expressed in terms of Antistreptolysin Units per ml, is given by the last container in which no red cell hemolysis has taken place.

For comparison purposes, there are compared in the following for the two methods, the drawbacks of the classical method and the advantages of the novel method described herein.

1. DRAWBACKS OF THE CLASSICAL METHOD 1.1 Fresh serum deprived of its complements is required, at 56° C. for 30 minutes (Initial blood sampling from the patient. Stay at room temperature during 2 hours. Separation of the coagulum from serum and centrifugation thereof. Inactivation of the serum complement at 56° C. during 30 minutes).

1.2 A number of dilutions must be carried out of the serum, which are to be distributed in containers with an addition of a constant quantity of O-streptolysin.

1.3 Necessity of having blood red cells of humans available (O Rh+) or of rabbits, washed and diluted to 5% (with the ensuing cumbersomeness of the washing steps).

1.4 Laboriousness of the procedure (addition of O-streptolysin and red cells to the diluted serum).

1.5 To carry out the classical titration, a certain number of thoroughly washed pipettes and test tubes is required.

2. ADVANTAGES OF THE NOVEL METHOD 2.1 No necessity of separating the serum, as the reaction can be conducted with the integral blood, which, inasmuch as a small quantity is required, can be drawn also from an ear lobe or a finger of the upper limbs.

2.2 A simple dilution of the sampled blood is made and a determined constant volume of it is distributed in each container (supplied by the producer and ready for use) which contains an appropriate quantity of toxin exactly metered by the producer, and different for each container. There is no necessity, thus, for the laborious dilutions and consequent distributions of serum as in the classical methods.

2.3 No addition is necessary of human and rabbit red cells, the result being no necessity of washings, since the reaction exploits in a direct manner the red cells as contained in the patient's blood.

2.4 The manipulations for determining the anti-O-streptolysin concentration are reduced to a minimum.

2.5 For the procedure no laboratory equipment is required, inasmuch as that which is necessary for the reaction can be contained—as to the cost and bulk—in the kit as supplied by the producer.

What I claim is:

1. A method for measuring the antistreptolysin concentration in a sample of human blood, comprising the steps of:

(a) preparing a plurality of solutions of different concentrations of oxidized O-streptolysin;

(b) preparing a solution of a reducing substance selected from the group consisting of thiols, sodium metabisulfite and sodium sulfite;

(c) diluting a blood sample with a nonhemolytic solution;

(d) introducing an equal volume of diluted blood in each of the solutions prepared in step (a);

(e) incubating the solutions prepared in step (d) at a temperature in the range between room temperature (18° C.–21° C.) and 50° C. for about 15 minutes;

(f) adding to the incubating solutions prepared in step (e) a measured volume of the solution prepared in step (b);

(g) incubating the solution prepared in step (f) at a temperature in the range between room temperature and 50° C. for sufficient time to cause the sedimentation of the red blood cells to occur, and (h) noting the sample containers in which no hemolysis has taken place.

*2. In a method for determining whether a detectable quantity of antistreptolysin is present in human blood, the steps which comprise:*

*(A) preparing a solution of a preselected concentration of oxidized O-streptolysin,*

*(B) preparing a solution of a reducing substance selected from the group consisting of thiols, sodium metabisulfite and sodium sulfite,*

*(C) preparing a blood sample for determination,*

*(D) introducing a measured quantity of said blood sample into the solution prepared in step (A),*

*(E) incubating the solution prepared in step (D) at a temperature and for a sufficient time to allow for the neutralization of the oxidized O-streptolysin should a detectable quantity of antistreptolysin be present in said blood,*

*(F) adding to the incubating solution prepared in step (E) a measured volume of the solution prepared in step (B),*

*(G) incubating the solution prepared in step (F) at a temperature and for a sufficient time to cause the sedimentation of the red blood cells to occur, and*

*(H) noting whether or not hemolysis has taken place therein.*

*3. The method of claim 2 wherein the incubation of the solution recited in step (E) is carried out at a temperature in the range between room temperature (18 deg. C.–21 deg. C.) and about 50 deg. C. for about 15 minutes.*

*4. The method of claim 2, wherein the incubation of solution recited in step (G) is carried out at a temperature in the range between room temperature and 50 deg. C.*

*5. The method described in claim 2*

*wherein the incubation of the solution recited in step (e) is carried out at a temperature in the range between room temperature (18° C.–21° C.) and about 50° C. for about 15 minutes, and*

*wherein the incubating of the solution recited in step (f) is carried out at a temperature in the range between room temperature and 50° C.*

* * * * *